(12) United States Patent
Nomoto et al.

(10) Patent No.: US 8,758,317 B2
(45) Date of Patent: Jun. 24, 2014

(54) ABSORBENT ARTICLE WITH SIDE GATHERS

(75) Inventors: Takashi Nomoto, Kanonji (JP); Masashi Uda, Kanonji (JP); Hideaki Morita, Kanonji (JP); Kenji Ohba, Kanonji (JP); Yuichi Suzuki, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 701 days.

(21) Appl. No.: 12/666,596

(22) PCT Filed: Jun. 23, 2008

(86) PCT No.: PCT/JP2008/061401
§ 371 (c)(1),
(2), (4) Date: Mar. 2, 2010

(87) PCT Pub. No.: WO2009/004940
PCT Pub. Date: Jan. 8, 2009

(65) Prior Publication Data
US 2010/0191209 A1    Jul. 29, 2010

(30) Foreign Application Priority Data
Jun. 29, 2007   (JP) ................. 2007-172430

(51) Int. Cl.
*A61F 13/15* (2006.01)
*A61F 13/20* (2006.01)

(52) U.S. Cl.
USPC .......... 604/385.101; 604/385.01; 604/385.04; 604/385.28

(58) Field of Classification Search
USPC ................... 604/385.04, 385.28, 385.01
See application file for complete search history.

(56) References Cited

U.S. PATENT DOCUMENTS

| 5,704,928 A | 1/1998 | Morita et al. |
| 2001/0020157 A1* | 9/2001 | Mizutani et al. ......... 604/385.04 |
| 2003/0028167 A1 | 2/2003 | Kashiwagi et al. |
| 2003/0120246 A1* | 6/2003 | Franklin et al. .......... 604/385.27 |
| 2007/0073259 A1* | 3/2007 | Erdman et al. ........... 604/385.28 |
| 2010/0174261 A1 | 7/2010 | Nomoto et al. |

FOREIGN PATENT DOCUMENTS

| EP | 1 132 069 | 9/2001 |
| JP | 4-325153 | 11/1992 |
| JP | 8-503638 | 4/1996 |
| JP | 11-19123 | 1/1999 |
| JP | 11-299821 | 11/1999 |
| JP | 2000-288025 | 10/2000 |
| JP | 2000-325395 | 11/2000 |
| JP | 2003-24384 | 1/2003 |
| JP | 2003-210525 | 7/2003 |
| JP | 2003-245306 | 9/2003 |
| JP | 2006-115957 | 5/2006 |
| JP | 2006-311939 | 11/2006 |
| WO | WO 94/12135 | 6/1994 |

OTHER PUBLICATIONS

International Search Report mailed Aug. 19, 2008, directed at International Application No. PCT/JP2008/061401; 2 pages.
International Search Report mailed Aug. 19, 2008, directed to International Application No. PCT/JP2008/061403; 2 pages.
Notice of Reasons for Rejection mailed Aug. 16, 2011, directed to Japanese Application No. 2011-135410; 3 pages.
Notice of Reasons for Rejection mailed Jan. 10, 2012, directed to Japanese Application No. 2011-135410; 3 pages.
Extended European Search Report mailed Feb. 1, 2012, directed to European Application No. 08777514.4; 4 pages.
Nomoto et al., U.S. Office Action mailed Aug. 30, 2012, directed to U.S. Appl. No. 12/666,550; 13 pages.
Nomoto et al., U.S. Office Action mailed Apr. 2, 2013, directed to U.S. Appl. No. 12/666,550; 12 pages.
Nomoto et al., U.S. Office Action mailed Aug. 16, 2013, directed to U.S. Appl. No. 12/666,550; 13 pages.
Office Action mailed Nov. 18, 2013, directed to TW Application No. 097124264; 7 pages.
Office Action mailed Jan. 3, 2014, directed to TW Application No. 097124263; 10 pages.

* cited by examiner

Primary Examiner — Melanie Hand
Assistant Examiner — Aundria Hairell
(74) Attorney, Agent, or Firm — Morrison & Foerster LLP

(57) ABSTRACT

An absorbent article that realizes favorable erection of gathers and excels in transversal leakage preventing effects. There is disclosed a vertically long absorbent article comprising a surface layer with surface sheet (2), a backside layer with backside sheet (3), an absorbent layer with absorbent body (4) interposed therebetween and a pair of gathers (5,5) formed of a sheetlike member (9) so as to have a hollow on both the side areas of the surface layer in the longitudinal direction thereof. The pair of gathers (5,5) in the state of having a three-dimensional configuration part (10) wherein the sheetlike member (9) makes a convex on the external surface side of the absorbent article in the thickness direction thereof are joined to the surface layer and/or backside layer by a junction portion (11) provided so as to extend in the longitudinal direction of the absorbent article. The three-dimensional configuration part (10) is provided so as to construct a hollow. The junction portion (11) includes a first junction edge portion (10*a*) defining the edge portion of the three-dimensional configuration part (10) on the inward side in the width direction thereof and a second junction edge portion (10*b*) defining the edge portion of the three-dimensional configuration part (10) on the outward side in the width direction thereof. Providing that L1 refers to the length of the three-dimensional configuration part (10) from the first junction edge portion (10*a*) to the second junction edge portion (10*b*) and L2 refers to the inter-junction-edge-portion distance being the distance between the first junction edge portion (10*a*) and the second junction edge portion (10*b*), the ratio thereof, L1/L2 is 2 or greater.

10 Claims, 11 Drawing Sheets

ABSORBENT ARTICLE WITH SIDE GATHERS

REFERENCE TO RELATED APPLICATION

This application is a national stage application under 35 USC 371 of International Application No. PCT/JP2008/061401, filed Jun. 23, 2008, which claims the priority of Japanese Application No. 2007-172430, filed Jun. 29, 2007, the contents of which prior applications are incorporated herein by reference.

FIELD OF THE INVENTION

The present invention relates to an absorbent article such as sanitary napkins, panty liners, disposable diaper and the like.

BACKGROUND OF THE INVENTION

Conventionally, as the absorbent article such as sanitary napkins, an elongated absorbent article is known, which includes a liquid-permeable surface layer; a liquid-impermeable back layer; and a liquid-retainable absorbent layer arranged between the surface layer and the back layer. Moreover, it is known to form gathers which stand up on the wearer's skin side in both sides of the absorbent article in order to improve the leakproof property in both sides in the longitudinal direction in such an absorbent article (see Japanese Unexamined Patent Application Publication No. 2000-288025, hereinafter referred to as Patent Document 1).

SUMMARY OF THE INVENTION

Problems to be Solved by the Invention

In the absorbent article as described in Patent Document 1, sheet members are arranged in both of the right and left side edge portions of the absorbent article, in which string-like elastic members are provided in a tensioned condition extending in the longitudinal direction over the entire longitudinal direction region of the absorbent article, and only perimeters of the sheet members are joined to the surface sheet and the back sheet, thereby providing a space between the sheet members and the surface sheet or the back sheet, and forming U-shaped gathers which stand up on the wearer's skin side as a result of shrinkage of the elastic members.

However, in the absorbent article as described in Patent Document 1, only the perimeters of the sheet members are joined to the surface sheet or the back sheet, and the sheet members are joined to the back sheet in the vicinity of the side edge portions in the longitudinal direction of the absorbent article, as a result of which the width of the region forming the space is wide. That is to say, in the absorbent article as described in Patent Document 1, the three-dimensional shape of the gathers is U-shaped or a shape in which the width is gradually increased from the top to the bottom of the gathers. As a result, when a force is applied to the absorbent article in the width direction, the three-dimensional shape of the gathers is easily deformed, thereby leading to a problem that the gathers are not stable when standing up and that the gathers with the three-dimensional shape tend to collapse. Moreover, there has been a problem that the effect of preventing side leakage was not sufficient due to the easy changing of the three-dimensional shape of the gathers.

Accordingly, an object of the present invention is to provide an absorbent article, which has a superior standability of the gathers, and which has a superior effect of preventing the side leakage.

Means for Solving the Problems

The present invention achieves the aforementioned object by providing an elongated absorbent article, which includes a surface layer; a back layer; an absorbent layer arranged between these; and a pair of gathers which are arranged in both sides of a longitudinal direction in the surface layer. Each of the pair of gathers is formed in such a way that the sheet member has a substantially Ω-shaped and three-dimensional-shaped portion, and that the three-dimensional-shaped portion is joined to the surface layer and/or the back layer by a connecting portion which is formed to extend in the longitudinal direction of the absorbent article, the three-dimensional-shaped portion configuring the hollow portion. The connecting portion includes a first connecting end and a second connecting end. In the three-dimensional-shaped portion, a ratio ($L1/L2$) of a length $L1$ from the first connecting end to the second connecting end and a distance between the first connecting end and the second connecting end is not less than 2.

More specifically, the present invention provides the following.

In a first aspect of an absorbent article of the present invention, the elongated absorbent article includes a surface layer having an at least partly liquid-permeable surface sheet; a back layer having a liquid-impermeable back sheet; an absorbent layer having a liquid-retainable absorbent body arranged between these; and a pair of gathers which are formed to be separated from each other in both sides along a longitudinal direction in the surface layer, and which are configured to have a hollow portion by a sheet member, in which each of the pair of gathers is formed in such a way that the sheet member has a three-dimensional-shaped portion which is convex on a skin contacting side of the absorbent article, and that the three-dimensional-shaped portion is joined to the surface layer and/or the back layer by a connecting portion which is formed to extend in the longitudinal direction of the absorbent article, the three-dimensional-shaped portion configuring the hollow portion, in which the connecting portion includes a first connecting end which forms an end inward in a width direction in the three-dimensional-shaped portion, and a second connecting end which forms an end outward in the width direction in the three-dimensional-shaped portion, and in which, in the three-dimensional-shaped portion, a ratio ($L1/L2$) of a length $L1$ from the first connecting end to the second connecting end and a distance $L2$ between the connecting ends, which is a distance between the first connecting end and the second connecting end, is not less than 2.

In a second aspect of the absorbent article as described in the first aspect of the present invention, the distance between the connecting ends at a side of both ends in the longitudinal direction of the absorbent article is greater than the distance between the connecting ends in a central portion in the longitudinal direction of the absorbent article.

In a third aspect of the absorbent article as described in the first or second aspect of the present invention, the connecting portion has a first connecting portion which is formed inward in the width direction of the absorbent article, and a second connecting portion which is formed more outward than the first connecting portion in the width direction, in which the first connecting end is formed in the first connecting portion, and the second connecting end is formed in the second connecting portion.

In a fourth aspect of the absorbent article as described in any one of the first to third aspects of the present invention, third connecting portions, which join the sheet member to the surface layer or the back layer more outward in the width direction than the connecting portion, are respectively formed at both ends of the longitudinal direction in the pair of gathers, in which a distance between an outer end in the third connecting portion and the first connecting end is longer than the distance between the connecting ends in the longitudinal direction of the central portion of the absorbent article.

In a fifth aspect of the absorbent article as described in any one of the first to fourth aspects of the present invention, the first connecting end is located in a region in which the surface layer is arranged on the absorbent layer, in which the second connecting end is located more outward in the width direction than an outer margin in the width direction of the absorbent layer.

In a sixth aspect of the absorbent article as described in any one of the first to fifth aspects of the present invention, each of the pair of gathers has a plurality of elastic members, in which the plurality of elastic members are arranged on a surface, or inside, the sheet member, and are arranged along the longitudinal direction.

In a seventh aspect of the absorbent article as described in the sixth aspect of the present invention, no less than two of the plurality of elastic members are arranged at an outer side, which is located outward in the width direction, among sides in the pair of gathers, in which the no less than two of the plurality of elastic members has a first elastic member, which is arranged the most closely to the second connecting end, and a second elastic member, which is adjacent to the first elastic member, and in which the second elastic member is located more outward in the width direction than the first elastic member.

In an eighth aspect of the absorbent article as described in any one of the sixth or seventh aspect of the present invention, each of the plurality of elastic members has a chromatic color, in which the chromatic color in each of the plurality of elastic members is visible through the sheet member.

In a ninth aspect of the absorbent article as described in any one of the sixth to eighth aspects of the present invention, each of the pair of gathers has a two-layered portion which is formed by folding back the sheet member, in which the plurality of elastic members are arranged in such a way to be interposed between layers of the two-layered portion.

In a tenth aspect of the present invention, a method of manufacturing an elongated absorbent article is provided, in which the absorbent article includes a surface layer having an at least partly liquid-permeable surface sheet; a back layer having a liquid-impermeable back sheet; an absorbent layer having a liquid-retainable absorbent body arranged between these; and a pair of gathers which are formed to be separated from each other in both sides along a longitudinal direction in the surface layer, and which is configured to have a hollow portion by a sheet member, in which each of the pair of gathers has a plurality of elastic members, and in which the plurality of elastic members are arranged along the longitudinal direction in an expanded state in the sheet member, the method including the steps of: conveying a pair of belt-shaped sheet members continuously with a predetermined interval in a width direction thereof; arranging elastic-members, in which the plurality of elastic-members are respectively arranged and adhered in an expanded state to an inner side of the pair of belt-shaped sheet members; two-folding, in which the pair of belt-shaped sheet members are folded back to one surface side in such a way that inner edges thereof are directed outward in a width direction, so as to sandwich the plurality of elastic members, thereby forming two-layered portions and single-layered portions outward in the width direction of the two-layered portions; three-folding, in which the two-layered portions are further folded back to the one surface side outward in the width direction, thereby forming three-layered portions; forming first connecting portions, in which the three-layered portions and the belt-shaped surface sheet are joined in a vicinity of an outer side of the width direction in the three-layered portions, thereby forming first connecting portions which extend in the longitudinal direction; and forming second connecting portions, in which the three-layered portions are folded back to another surface side outward in the width direction with the first connecting portions as starting points, and at least the bottom layers in the folded-back three-layered portions are joined to the single-layered portions, thereby forming second connecting portions.

Effects of the Invention

According to the absorbent article of the present invention, the standability of the gathers is superior, and the effect of preventing the side leakage is superior.

EXPLANATION OF REFERENCE NUMERALS

Figure 1:
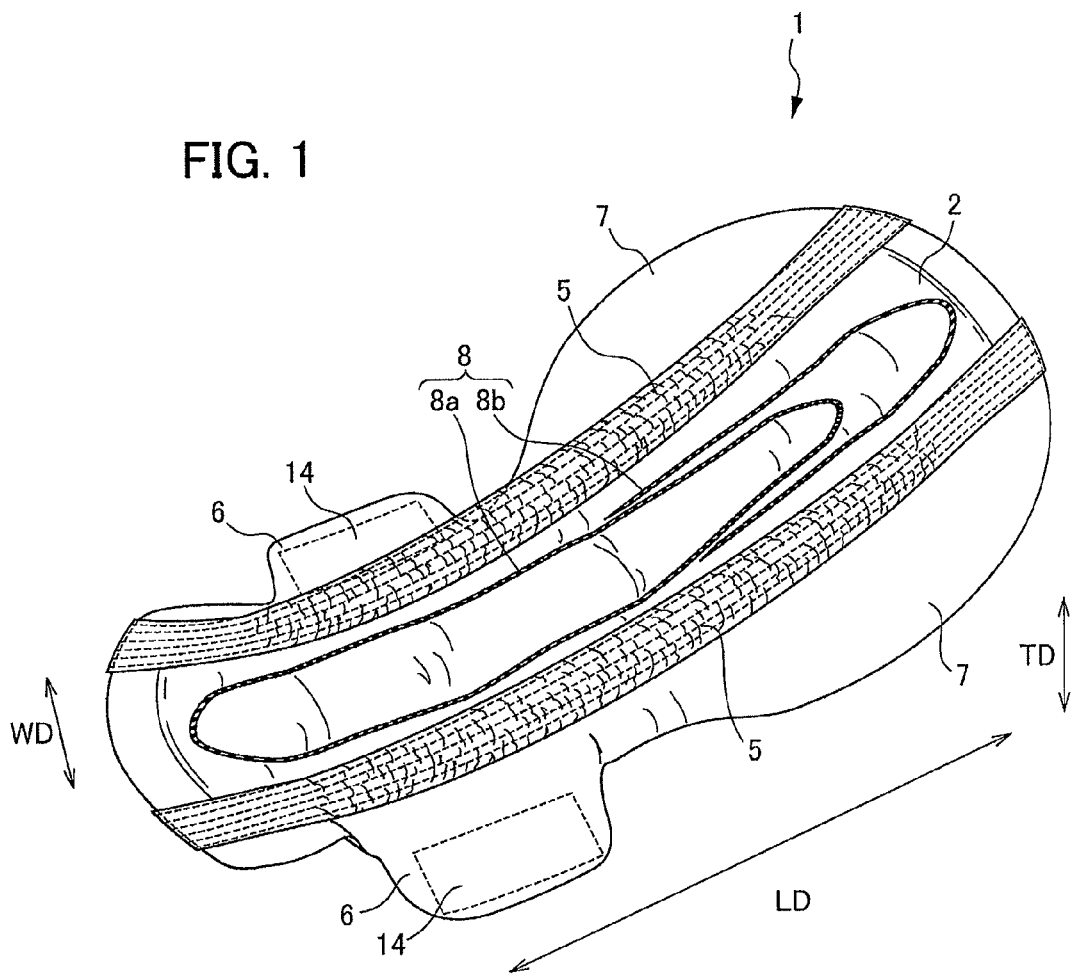
FIG. 1 is a perspective view of a sanitary napkin in a natural state as one embodiment of the absorbent article of the present invention.

1 Sanitary Napkin
2 Surface sheet
3 Back sheet
4 Absorbent body
5 Gather
6 Wing
7 Posterior flap
8 Groove portion
9 Sheet member
10 Dimensional-shaped portion
11 Connecting portion
12 Third connecting portion
13 Elastic member

DETAILED DESCRIPTION OF THE INVENTION

Figure 2:
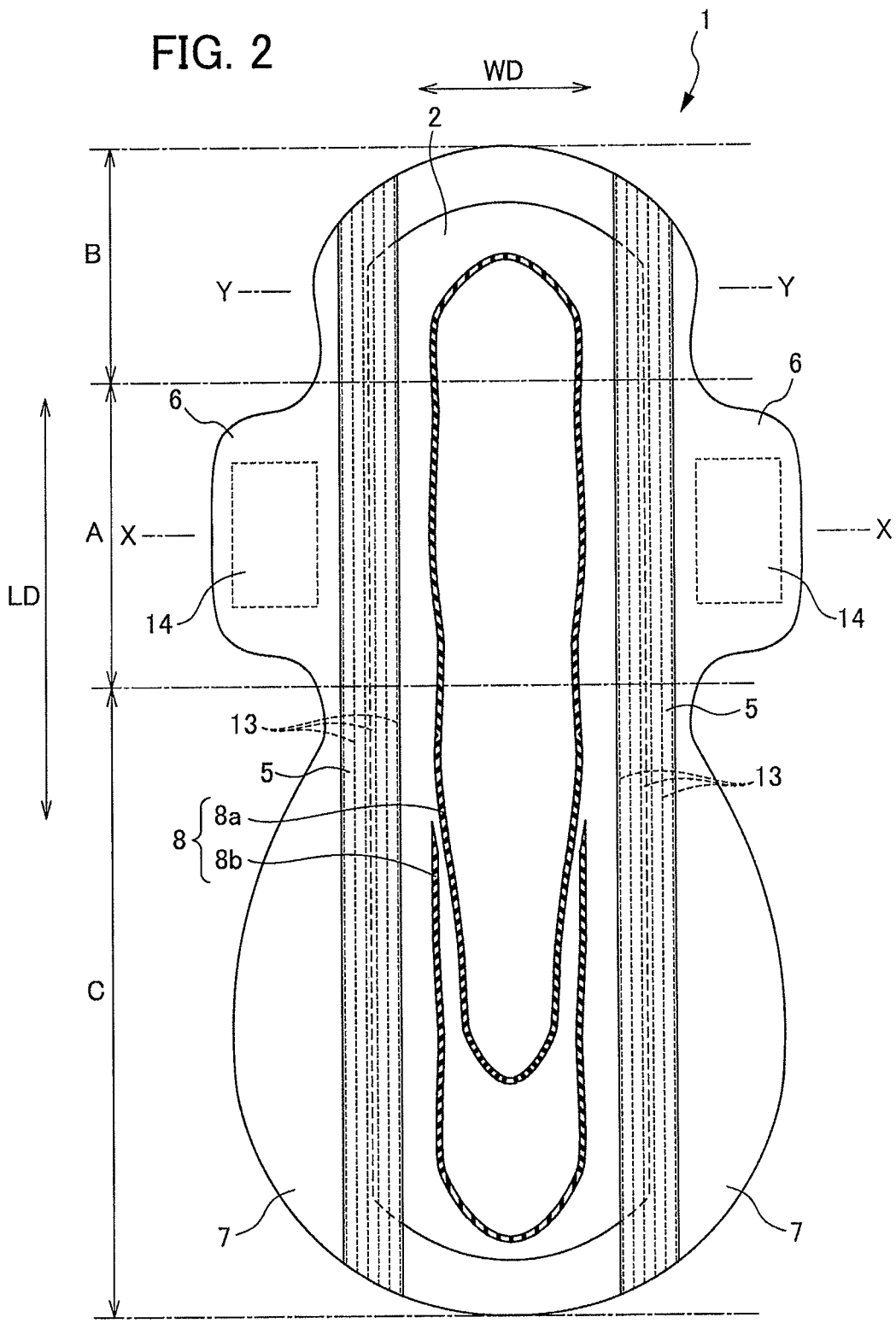
FIG. 2 is a plan view of the sanitary napkin shown in FIG. 1, when observed from the surface sheet side in a natural state.
Figure 3:
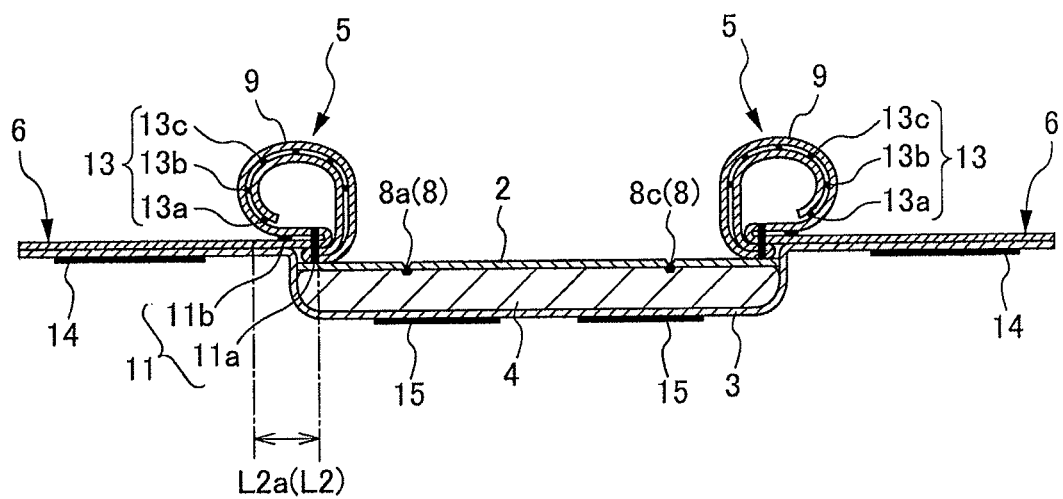
FIG. 3 shows a cross sectional view of FIG. 2 taken along the line X-X.

Hereinafter, a preferred embodiment of the present invention is explained with reference to the drawings. The absorbent article of the present embodiment is a sanitary napkin 1, has an elongated shape as shown in FIGS. 1 to 3, and at least a part thereof as a surface layer is provided with a liquid-permeable surface sheet 2; a liquid-impermeable back sheet 3 as a back layer; and an absorbent body 4 as a liquid-retainable absorbent layer arranged between them in an interposing way. A pair of gathers 5 and 5 are arranged in both sides of the longitudinal direction to the side of a surface sheet 2 of the sanitary napkin 1, in such a way that the pair of gathers are separated from each other, and have hollow portions formed by sheet members 9. The pair of gathers 5 and 5 stand up on the skin contacting side in the vicinity of the side edges of the absorbent body 4.

The surface layer is a layer constituting a face of the side abutting the skin of the wearer at the time of wearing the absorbent article, and, in the present embodiment, the surface layer includes the surface sheet 2 and sheet members 9. Moreover, the surface layer includes a second sheet (not shown) arranged between the surface sheet and the absorbent body.

The back layer is a layer constituting a face of the non-skin contacting side of the absorbent article, and, in the present embodiment, the back layer includes the back sheet 3.

The absorbent layer includes the absorbent body 4 and a core-wrapping material (not shown) covering the absorbent body 4.

As shown in FIG. 2, the sanitary napkin 1 has a central portion A which is a portion opposed to the wearer's excretion part at the time of the wearing; an anterior portion B which is arranged more ventrally than the central portion A, to the wearer, at the time of the wearing; and a posterior portion C which is arranged more dorsally than the central portion A at the time of the wearing.

As shown in FIG. 2 and FIG. 3, the surface sheet 2 covers the entire area of the top surface of the absorbent body 4. The back sheet 3 covers the entire area of the under surface of the absorbent body 4. The back sheet 3 extends outward in the width direction from the side edges of the absorbent body 4 in the position of the central portion A, thereby forming part of a pair of wings 6 and 6. Moreover, the back sheet 3 extends outward in the width direction from the side edges of the absorbent body 4 in the position of the posterior portion C as well, thereby forming part of a pair of posterior flaps 7 and 7. In addition, in the central portion A and the posterior portion C, the sheet members 9, which form a pair of gathers 5 and 5 to be described later, respectively extend outward in the width direction, thereby forming part of the pair of wings 6 and 6 and part the pair of posterior flaps 7 and 7. The pair of wing 6 and 6 and the pair of posterior flaps 7 and 7 are formed by joining the sheet members 9 and the back sheet 3. The surface sheet 2 and the back sheet 3 extend from the front edge and the rear edge of the absorbent body 4, and are joined to each other in the extended portions.

Figure 4:
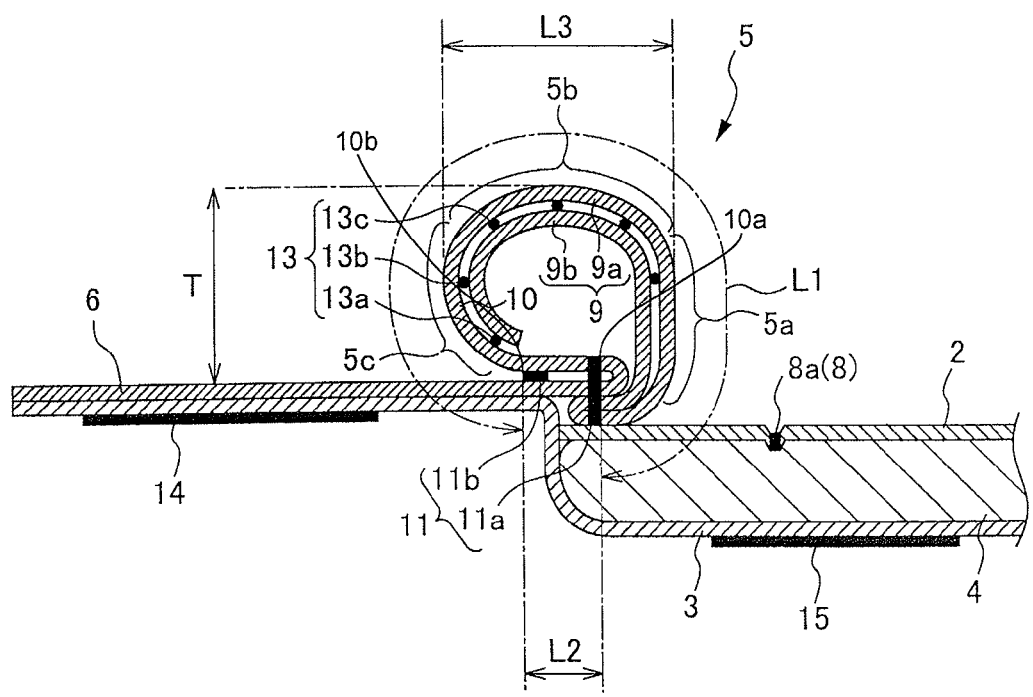
FIG. 4 is a partially enlarged view of FIG. 3.

As shown in FIG. 3 and FIG. 4, wing adhesive parts 14 and 14 are provided to the under surface side of the back sheet in the pair of wings 6 and 6 respectively. Moreover, main-body adhesive parts 15 are provided to the under surface side of the back sheet 3 in the main-body portion (the region in which the absorbent body 4 is arranged) of the sanitary napkin 1. The main-body adhesive parts 15 are provided in two lines extending in the longitudinal direction of the sanitary napkin 1.

The wing adhesive parts 14 and the main-body adhesive parts 15 are formed by applying a hot melt adhesive to the under surface side of the back sheet 3.

As shown in FIG. 3, leak-proof groove portions 8 are provided to the surface sheet side of the absorbent body 4, the absorbent body 4 and the surface sheet being compacted and consolidated into the leak-proof groove portions 8. As shown in FIG. 2, the pair of gathers 5 and 5 are located outward in the width direction of the leak-proof groove portions 8. The shape of the leak-proof groove portions 8 is substantially symmetrical about a longitudinal centerline (not shown) of the sanitary napkin 1. In the present embodiment, the leak-proof groove portions 8 include a first leak-proof groove portion 8a which is provided in a range from the anterior portion B to the posterior portion C, and a second leak-proof groove portion 8b which is provided in the posterior portion C. The first leak-proof groove portion 8a has an elongated circular shape. Moreover, as shown in FIG. 2, the first leak-proof groove portion 8a has, in the central portion A, a shape that is convexly curved outward in the width direction. The second leak-proof groove portion 8b is provided outward the first leak-proof groove portion 8a, and has a shape that is convexly curved backward. The front ends of the second leak-proof groove portion 8b are located in the vicinity of the first leak-proof groove portion 8a, but are not joined to the first leak-proof groove portion 8a.

As shown in FIG. 3 and FIG. 4, the pair of gathers 5 and 5, which are arranged in both sides of the sanitary napkin 1, are formed from the sheet members 9. As for the pair of gathers 5 and 5, each of the sheet members 9 has a three-dimensional-shaped portion 10 which is outwardly convex in the width direction on the skin contacting side in the sanitary napkin 1, and the three-dimensional-shaped portion 10 is joined to the surface layer and/or the back layer with a connecting portion 11 which is formed to extend in the longitudinal direction of the sanitary napkin 1. This three-dimensional-shaped portion 10 is configured such that a hollow portion is provided inside thereof, thereby forming the gather 5 having a three-dimensional shape.

As shown in FIG. 4, the connecting portion 11 includes a first connecting end 10a which forms an end inward in the width direction in the three-dimensional-shaped portion 10, and a second connecting end 10b which forms an end outward in the width direction in the three-dimensional-shaped portion 10. Moreover, in the three-dimensional-shaped portion 10, the ratio (L1/L2) of the length L1 from the first connecting end 10a to the second connecting end 10b and the distance L2 between the connecting ends, which is the distance between the first connecting end 10a and the second connecting end 10b, is not less than 2, preferably between 2 to 15 inclusive, and more preferably between 5 to 11 inclusive.

Furthermore, as shown in FIG. 4, the cross-sectional shape of the gather 5 in the width direction is substantially Ω-shaped, in which the largest width L3 of the three-dimensional shape of the gathers 5 is greater than the distance L2 between the connecting ends.

In the present specification, as shown in FIG. 4, the substantial Ω-shape includes a shape in which the largest width L3 of the three-dimensional shape of the gather 5 is greater than the length L2 between the connecting ends in the cross-sectional shape of the gather 5 in the width direction, and includes, for example, a shape in which the cross-sectional shape of the gather is inclined outward or inward in the width direction.

Moreover, the substantial Ω-shape in the present specification also includes a shape in which only a portion forming the three-dimensional-shaped portion 10 in the gather 5, i.e. only a portion constituting the skin contacting side excepting the connecting portion 11, is formed with the sheet member 9.

In cases where the ratio of the length L1 from the first connecting end 10a to the second connecting end 10b in the three-dimensional-shaped portion 10 in relation to the length L2 between the connecting ends (the first connecting end 10a and the second connecting end 10b) is less than 2, the gather 5 cannot form a three-dimensional shape having a sufficient hollow portion, thereby making it impossible to obtain a superior effect of preventing side leakage.

In the present embodiment, as shown in FIG. 3 and FIG. 4, the connecting portion 11 includes a first connecting portion 11a which is formed inward in the width direction of the sanitary napkin 1, and a second connecting portion 11b which is formed more outward than the first connecting portion in the width direction. The first connecting end 10a is formed in the first connecting portion 11a, and the second connecting end 10b is formed in the second connecting portion 11b.

The first connecting portion 11a is formed by a heat embossing process which joins the sheet member 9 and the surface sheet 2. The second connecting portion is formed in such a way that the folded parts of the sheet member 9 are joined each other with a hot-melt adhesive.

Moreover, as shown in FIG. 4, in the pair of gathers 5 and 5, the first connecting end 10a is located in a region where the surface sheet 2 is arranged on the absorbent body 4, and the second connecting end 10b is located in a region, in the back sheet 3, outward to the external margin of the absorbent body 4 in the width direction. The case where the second connecting end 10b is located in the region in the back sheet 3 includes not only a case where the second connecting end 10b is formed by joining the sheet member 9 and the back sheet 3, but also a case where the second connecting end 10b is formed by joining the sheet member 9 arranged on a top surface of the back sheet 3, or joining another seat and the sheet member 9.

Figure 6:
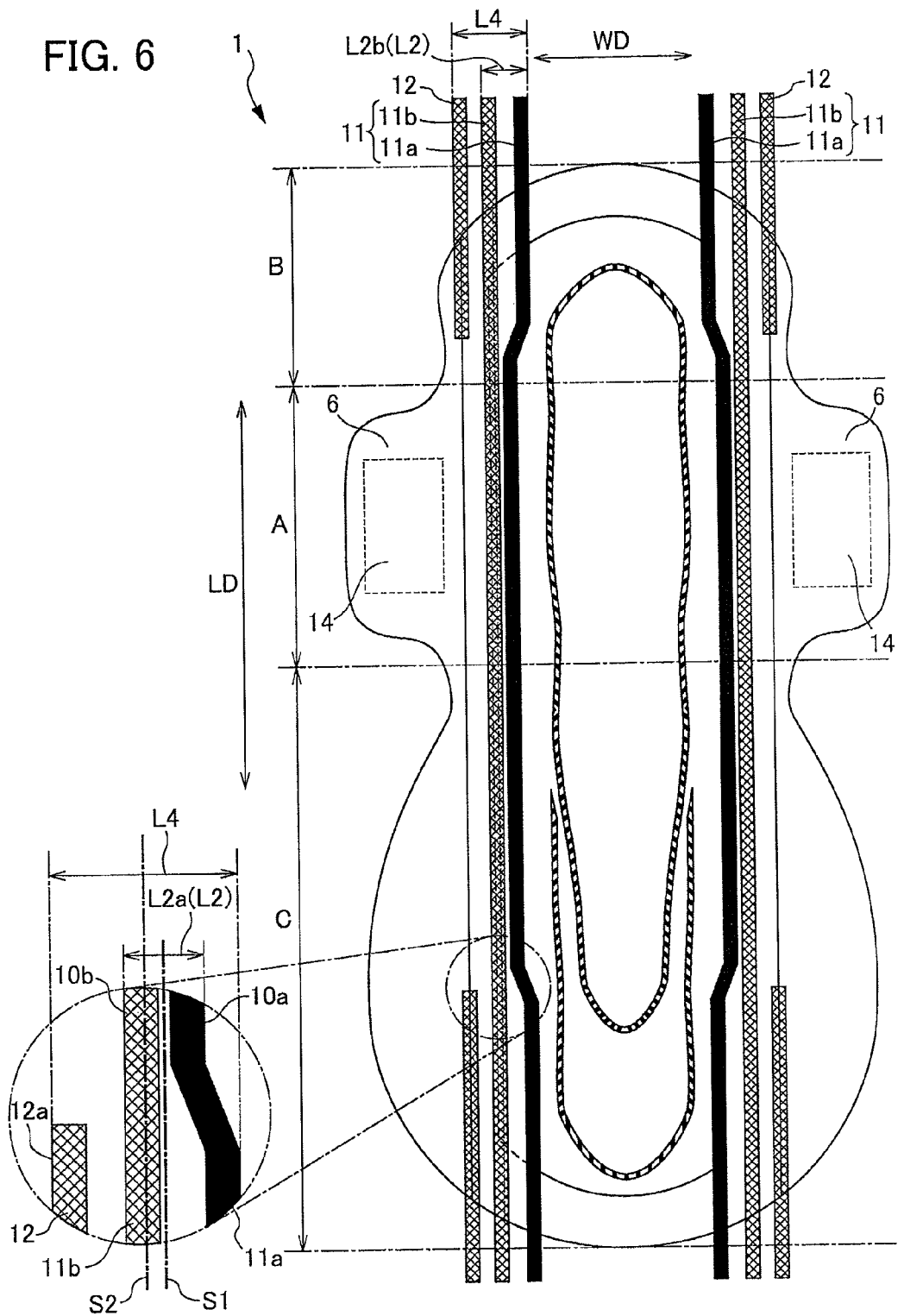
FIG. 6 is a diagram for showing an arrangement of a first connecting portion, a second connecting portion and a third connecting portion, in the absorbent article shown in FIG. 1.

The distance L2b between the connecting ends at both ends in the longitudinal direction of the sanitary napkin 1 is greater than the distance L2a between the connecting ends in the central portion A in the longitudinal direction of the sanitary napkin 1 (see FIG. 6). Specifically, from the viewpoint of increasing the stability of the gathers 5 at the time of standing up, it is preferable that the length L2b between the connecting ends at both ends in the longitudinal direction of the sanitary napkin 1 be 1 to 26 mm greater than the distance L2a between the connecting ends in the central portion A in the longitudinal direction of the sanitary napkin 1.

Figure 5:
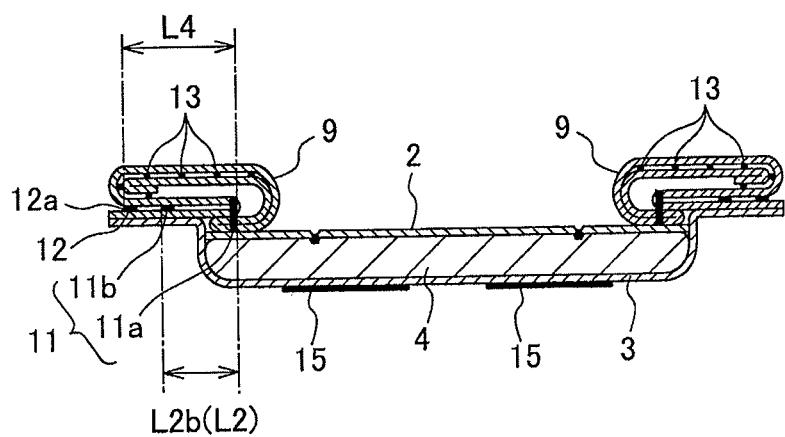
FIG. 5 is a cross-sectional view of FIG. 2 taken along the line Y-Y.

As shown in FIG. 5, third connecting portions 12, which join the sheet members 9 to the surface layer or the back layer outward the connecting portion 11, are respectively formed at both ends of the longitudinal direction the pair of gathers 5 and 5. The distance L4 between an outer end 12a in the third connecting portion 12 and the first connecting end 10a is longer than the distance L2a between the connecting ends in the longitudinal direction of the central portion A of the sanitary napkin 1 (see FIG. 6). In the present embodiment, as shown in FIG. 5, the third connecting portion 12 is formed in such a way that the sheet members 9 are joined to each other more outward than the second connecting portion 1ib in the width direction by using a hot-melt adhesive.

In the present embodiment, since the pair of gathers 5 and 5 are joined to the surface layer by the third connecting portions 12 at the front edge and the rear edge of the longitudinal direction, the pair of gathers 5 and 5 do not have a three-dimensional shape without standing up in the front edge and the rear edge. That is to say, the pair of gathers 5 and 5 are planar at both ends of the longitudinal direction of the sanitary napkin 1. In a region between the front edge and the rear edge of the longitudinal direction of the sanitary napkin 1, in which the third connecting portions 12 are not provided, the pair of gathers 5 and 5 stand up on the skin contacting side, thereby forming a hollow three-dimensional shape.

The range, in which the third connecting portions 12 are formed, substantially corresponds to the region having the distance L2b between the connecting ends at both ends of the longitudinal direction of the sanitary napkin 1.

It is preferable that the range having the distance L2b between the connecting ends at both ends of the longitudinal direction of the sanitary napkin 1, i.e. the range in which the third connecting portions are formed, be the range of 40 to 70 mm from the front end in the anterior portion B of the sanitary napkin 1. Moreover, it is preferable that the range be 70 to 120 mm from the rear end in the posterior portion C.

In cases where the range, in which the third connecting portions 12 are formed, is less than 40 mm from the front end in the anterior portion B of the sanitary napkin 1, and in cases where the range is less than 70 mm from the rear end in the posterior portion C, the length of the standing portion of the gathers 5 having a three-dimensional shape becomes longer, thereby it is apprehended that the gathers 5 tend to collapse. Moreover, it is apprehended that, in the posterior portion C, the gathers 5 having a three-dimensional shape collide with the buttocks of the wearer, thereby causing uncomfortability.

In cases where the range, in which the third connecting portions 12 are formed, is more than 70 mm from the front end in the anterior portion B of the sanitary napkin 1, and in cases where the range is more than 120 mm from the rear end in the posterior portion C, the length of the standing portion of the gathers 5 having a three-dimensional shape becomes shorter, and the standability of the gathers 5 is decreased, thereby it is apprehended that the fitness while in use is decreased.

Moreover, as shown in FIG. 6, a center S1 in the width direction of the connecting portion 11 in the central portion A in the longitudinal direction of the sanitary napkin 1 is located more inward in the width direction than a center S2 between the outer end 12a in the third connecting portion 12 and the first connecting end 10a. Specifically, it is preferable that the center S1 in the width direction of the connecting portion 11 be located inward in the width direction, by approximately between 0.5 to 13 mm inclusive, in relation to the center S2 between the outer end 12a in the third connecting portion 12 and the first connecting end 10a.

A plurality of elastic members 13 are respectively arranged to the pair of gathers 5 and 5. The plurality of elastic members 13 are arranged on the surface of, or inside, the sheet members 9 with predetermined intervals along the longitudinal direction of the sanitary napkin 1. The plurality of elastic members 13 are joined, in an expanded state, to the sheet members 9 by using a hot-melt adhesive. When the plurality of elastic members 13 are joined to the sheet members 9, it is preferable that the joining to the sheet members 9 be performed by applying the hot-melt adhesive to the plurality of elastic members 13, from the viewpoint of reducing the coated area of the hot-melt adhesive and of improving the touch.

In the present embodiment, as shown in FIG. 3 to FIG. 5, six of the plurality of elastic members 13 are arranged to each of the pair of gathers 5 and 5, and the plurality of elastic members 13 are respectively arranged along the longitudinal direction with substantially equal intervals in the width direction of the sheet members 9. As shown in FIG. 4, the plurality of elastic members are arranged to all of an inner side 5a, a top side 5b and an outer side 5c in the three-dimensional shape of the pair of gathers 5 and 5.

As shown in FIG. 4, among the plurality of elastic members 13 which are arranged to the outer side 5c, the first elastic member 13a which is arranged in the nearest location to the second connecting end 10b is located more inward in the width direction of the sanitary napkin 1 than the second elastic member 13b which is adjacent to the first elastic member 13a. Moreover, the third elastic member 13c, which is adjacent to the second elastic member 13b, is located more inward in the width direction of the sanitary napkin 1 than the second elastic member 13b. That is to say, the second elastic member 13b is located in the outermost position in the width direction, and the first elastic member 13a and the third elastic member 13c, which are adjacent to the second elastic member 13b, are located inward thereof.

The plurality of elastic members 13 are arranged in the outer side 5c in this way, as a result of which the sanitary napkin 1 of the present embodiment makes it possible to maintain the substantial Ω-shape of the gather 5 in a stable state.

Moreover, since the first elastic member 13a and the third elastic member 13c, which are adjacent to both sides of the second elastic member 13b, are located inward in the width direction of the second elastic member 13b, resistance to forces from the width direction is increased regarding the gathers 5 of the present embodiment. Accordingly, even in cases where the sanitary napkin 1 receives forces in the width direction, the gathers 5 having a three-dimensional shape are hard to collapse.

The sanitary napkin 1 of the present embodiment has a shape that is concavely curved on the skin contacting side in the longitudinal direction in a natural state, because of the contractive force of the plurality of elastic members 13 which are arranged in an expanded state in the sheet members 9. It should be noted that the natural state refers to a state where no external forces other than the gravity are acting on the sanitary napkin 1

It should also be noted that at least part of the plurality of elastic members 13 is preferably arranged to the inner side 5a or the outer side 5c which are sides of the pair of gathers 5 and 5, from the viewpoint of maintaining the three-dimensional shape of gathers 5 in a stable state.

From the viewpoint of maintaining the three-dimensional shape of the gathers 5 in a superior state, the interval of the plurality of elastic members 13 is preferably between 3 to 10 mm inclusive, and more preferably between 4 to 7 mm inclusive.

From the viewpoint of maintaining the three-dimensional shape of the gathers 5 in a stable state, the number of the plurality of elastic members, which are arranged to the sheet members 9, is preferably between 4 to 10 inclusive. In cases where the number of the elastic members 13 is not more than three, it is hard to form the substantial Ω-shape, thereby it is apprehended that it becomes hard to achieve the effect of preventing the side leakage. In cases where the number of the elastic members 13 is not less than 11, the rigidity of the gathers 5 is increased, thereby it is apprehended that the touch is deteriorated.

It is preferable that the tension, which is applied when the plurality of elastic members 13 are arranged to the sheet members 9, be gradually increased from the top side 5b to the inner side 5a and the outer side 5c in the gather 5 having a three-dimensional shape. The tension is gradually increased from the top side 5b to the inner side 5a and the outer side 5c, thereby making it possible to configure the gathers 5 which are less likely to collapse due to the forces in the width direction.

Moreover, it is preferable that the difference of the tension of the plurality of elastic members 13 to be arranged be within 300 gf/25 mm.

Each of the plurality of elastic members 13 has a chromatic color, and the chromatic color in each of the plurality of elastic members 13 is visible through the sheet members 9. In the present embodiment, each of the plurality of elastic members 13 uses blue as the chromatic color. The color of the plurality of elastic members 13 is not particularly limited as long as it is not white, but it is preferably a color which achieves visibility as well as a feeling of cleanliness.

From the viewpoint that the chromatic color of the elastic members 13 should be easily visible through the sheet members 9, the color of the sheet members 9 is preferably transparent, semitransparent, white, etc. which are likely to transmit the chromatic color.

In this way, since the plurality of elastic members 13 having a chromatic color are visible through the sheet members 9 in the gathers 5 having a three-dimensional shape, even such a gather, in which free ends are not formed, as in the present embodiment gives the wearer a three-dimensional impression of a convex three-dimensional structure at the skin contacting side. This provides the feeling of security (security against the side leakage) regarding the sides of the sanitary napkin 1, as a result of which the wearer is provided with the feeling of security regarding the sanitary napkin 1 itself.

As shown in FIG. 4, each of the pair of gathers 5 and 5 has a two-layered portion which is formed by folding back the sheet members 9. The plurality of elastic members 13 are arranged in such a way to be interposed between an outer layer 9a and in inner layer 9b in the two-layered portion.

In the present embodiment, the two-layered portion is formed in an entire area of the inner side 5a, an entire area of the top side 5b, and an upper area of the outer side 5c in the gather 5. All of the six elastic members 13 are arranged in such a way to be interposed between the outer layer 9a and the inner layer 9b in the two-layered portion. The outer layer 9a and the inner layer 9b are joined by means of a hot-melt adhesive applied to the plurality of elastic members 13.

It is preferable that the gathers 5, which include the sheet members 9 and the plurality of elastic members 13, have appropriate rigidity from the viewpoint of maintaining the hollow three-dimensional shape in a stable state and of obtaining a superior feeling of wearing. However, if the rigidity is too high, the feeling while in use may be deteriorated.

Moreover, as for the physical properties of the expansion and contraction of the gathers 5, a stress at the time when the gather 5 is extended 5 to 50% in the longitudinal direction of the sanitary napkin 1 is preferably 50 to 500 gf/25 mm width, and more preferably 100 to 300 gf/25 mm width. In cases where the stress is less than 50 gf/25 mm width, the expansion and contraction force of the gathers 5 is weak, thereby it is apprehended that the standability of the gathers 5 is deteriorated. In cases where the stress is more than 500 gf/25 mm width, the degree of the curve in the longitudinal direction of the sanitary napkin 1 is high, thereby it is apprehended that the fitness with the wearer's body is decreased.

The preferable range of numerical values in each configuration of the sanitary napkin of the present embodiment is described below.

The length L1 of the sheet members 9 from the first connecting end 10a to the second connecting end 10b in the three-dimensional-shaped portion 10 is preferably 30 to 58 mm, and more preferably 16 to 58 mm, from the viewpoint of securing the standing height of the gathers 5. The standing height of the gathers 5 is preferably 15 to 25 mm, and more preferably 10 to 30 mm. In cases where the standing height T of the gathers 5 is less than 10 mm, it is apprehended that the effect of preventing the side leakage is decreased, and that the wearer is not provided with the feeling of security that enough function of preventing the side leakage is given. In cases where the standing height T of the gathers 5 is higher than 30 mm, it is apprehended that the fitness to the wearer's body by the gathers 5 is excessively strong, and that the fitness between the absorbent body 4 and the wearer's body is decreased.

From the viewpoint of forming the gathers 5 with superior standability, the distance L2 between the connecting ends, which is the distance between the first connecting end 10a and the second connecting end 10b, is preferably 5 to 20 mm, and more preferably 5 to 15 mm. In cases where the distance L2 between the connecting ends is less than 2 mm, it is apprehended that the gathers 5 are likely to collapse due to the forces applied from the width direction of the sanitary napkin 1. In cases where the gathers 5 collapse in this way, it is apprehended that the collapsed gathers 5 cover the absorption face of the absorbent body 4. In cases where the distance L2 between the connecting ends exceeds 20 mm, the hollow portion is hard to be formed in the gather 5, and a gap is likely to be caused between the gathers 5 and the wearer's body, thereby it is apprehended that the leak-proof effect is decreased. From the viewpoint of preventing the gathers 5 from easily deforming due to the forces applied from the width direction of the sanitary napkin 1, the maximum width L3 in the three-dimensional shape of the gathers 5 needs to be greater than the distance L2 between the connecting ends, which is the distance between the first connecting end 10a and the second connecting end 10b, and is specifically preferably 5 to 38 mm, and more preferably 6 to 30 mm.

The distance L4 between the outer end 12a in the third connecting portion 12 and the first connecting end 10a is preferably 25 to 35 mm. In cases where the distance L4 between the outer end 12a in the third connecting portion 12 and the first connecting end 10a is more than 35 mm, the contact area of the skin of the wearer and the sheet members 9 constituting the gathers 5 becomes wide, thereby it is apprehended that a feeling of wearing is deteriorated.

The method of manufacturing the sanitary napkin 1 of the present embodiment is described below based on one preferred embodiment with reference to FIG. 7 to FIG. 11.

The method of manufacturing the sanitary napkin 1 of this embodiment has the following steps (a) to (g).
(a) conveying step
(b) elastic-member arranging step
(c) two-folding step
(d) three-folding step
(e) first-connecting-portion forming step
(f) second-connecting-portion forming step
(g) third-connecting-portion forming step (a) Conveying Step In the conveying step, a pair of belt-shaped sheet members 902 and 902 are continuously conveyed with a predetermined interval in the width direction.

(b) Elastic-Member Arranging Step

In the elastic-member arranging step, the plurality of elastic members 13 are respectively arranged and adhered, in an expanded state, to the vicinity of the inner side of the pair of belt-shaped sheet members 902 and 902 which have been conveyed.

Figure 7A:
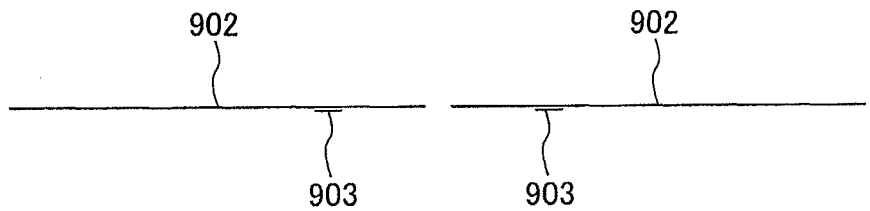
FIG. 7A shows a pair of sheet members in a state where an auxiliary hot-melt adhesive has been applied in an elastic-member arranging step.

In this embodiment, as shown in FIG. 7A, an auxiliary hot-melt adhesive 903, which assists the formation of the first connecting portion 11a in the first-connecting-portion forming step to be described later, is applied to an under surface in the locations with a predetermined space from inner edges of the pair of belt-shaped sheet members 902 and 902. Subsequently, the plurality of elastic members 13 are arranged in an expanded state to the outward of the width direction of the region to which the auxiliary hot-melt adhesive 903 has been applied. The hot-melt adhesive (not shown) is applied to each of the plurality of elastic members 13 with a means for applying adhesive (not shown), before the plurality of elastic members 13 are arranged to the belt-shaped sheet members 902. The plurality of elastic members 13, in a state where the hot-melt adhesive has been applied thereto, are then arranged to the belt-shaped sheet members 902.

(c) Two-Folding Step

In the two-folding step, the pair of belt-shaped sheet members 902 and 902 are folded back to one surface side in such a way that the inner edges thereof are directed outward in the width direction, so as to sandwich the plurality of elastic members 13, thereby forming two-layered portions 904 and single-layered portions 905 outward in the width direction of the two-layered portions.

Figure 7B:
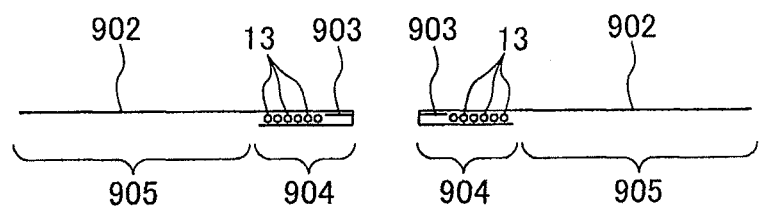
FIG. 7B shows a pair of sheet members in a two-folding step.

In the present embodiment, as shown in FIG. 7B, portions, which are more inward to the inner edges of the regions in which the hot-melt adhesive 903 has been applied to the pair of belt-shaped sheet members 902 and 902 in the elastic-member arranging step, are folded back to the under surface side with a two-folding means (not shown) in such a way to sandwich the plurality of elastic members, thereby forming the two-layered portions 904. Moreover, the single-layered portions 905 are formed outward in the width direction of the two-layered portions 904. Here, the hot-melt adhesive has been applied to the plurality of elastic members 13, and the belt-shaped sheet members 902 constituting the two-layered portions 904 are joined to each other with the plurality of elastic members 13 interposed therebetween.

(d) Three-Folding Step

In the three-folding step, the two-layered portions 904 are further folded back to one surface side outward in the width direction, thereby forming three-layered portions 906.

Figure 7C:
FIG. 7C shows a pair of sheet members in a three-folding step.

In the present embodiment, as shown in FIG. 7C, the two-layered portions 904 are further folded back to the under surface side outward in width direction with a three-folding means 105, thereby forming three-layered portions 906. Moreover, the single-layered portions 905 are provided outward in the width direction of the three-layered portions 906.

(e) First-Connecting-Portion Forming Step

In the first-connecting-portion forming step, the three-layered portions 906 and belt-shaped surface sheet 200 are joined in the vicinity of the outer side of the width direction in the three-layered portions 906, thereby forming the first connecting portions 11a which extend in the longitudinal direction.

Figure 8A:
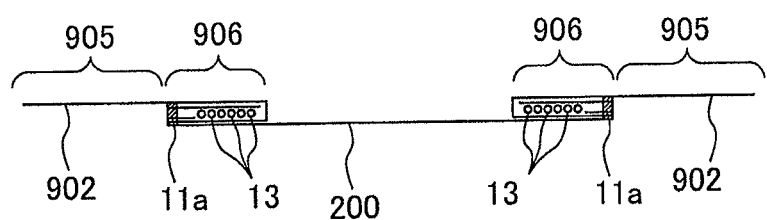
FIG. 8A shows a central portion of the sanitary napkin in a first-connecting-portion forming step.
Figure 8B:
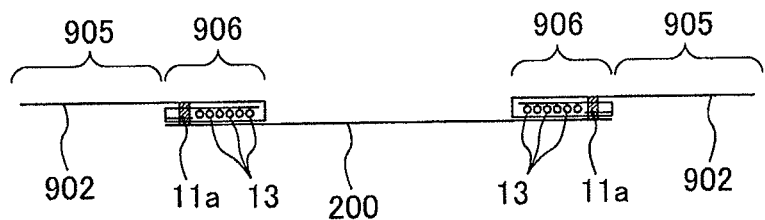
FIG. 8B shows the vicinity of a front edge of the sanitary napkin in the first-connecting-portion forming step.

In the present embodiment, as shown in FIG. 8B and FIG. 8B, the pair of belt-shaped sheet members 902 and 902 having the three-layered portions 906 and the single-layered portions 905 are disposed to both sides of the width direction on the top surface of the belt-shaped surface sheet 200, in such a way that the three-layered portions 906 are laminated on the belt-shaped surface sheet 200 and the single-layered portions 905 are directed outward in the width direction. The laminated belt-shaped surface sheet 200 is joined to the belt-shaped sheet members 902 and 902 with a sealing means (not shown), thereby forming the first connecting portions 11a.

The first connecting portions 11a are formed by heat sealing. Moreover, the auxiliary hot-melt adhesive 903, which assists the formation of the first connecting portions 11a, has been applied to the belt-shaped sheet members 902 in the regions in which the first connecting portions 11a are formed. The first connecting portions 11a are also joined by the adhesive force of this auxiliary hot-melt adhesive 903. Moreover, as shown in FIG. 6, the first connecting portions 11a are formed more outward in the region in which the central portion of the longitudinal direction of the sanitary napkin 1 is located, than in the regions in which the vicinities of both ends of the longitudinal direction of the sanitary napkin 1 are located.

(f) Second-Connecting-Portion Forming Step

In the second-connecting-portion forming step, the three-layered portions 906 are folded back to the other surface side outward in the width direction with the first connecting portions 11a as starting points, and at least the bottom layers in the folded-back three-layered portions 906 are joined to the single-layered portions 905, thereby forming the second connecting portions 11b.

Figure 9A:
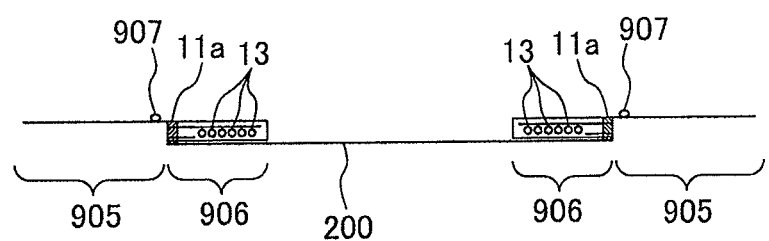
FIG. 9A shows the central portion of the sanitary napkin in a state where a hot-melt adhesive for forming a second connecting portion has been applied in a second-connecting-portion forming step.
Figure 9B:
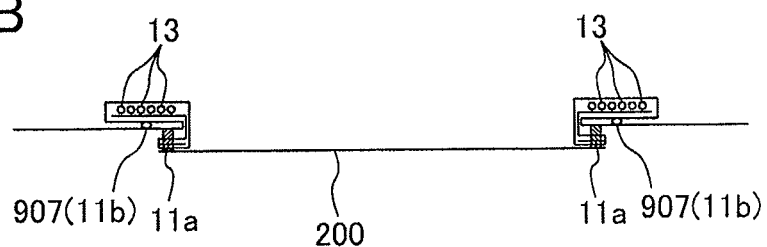
FIG. 9B shows the central portion of the sanitary napkin in a state where a three-layered structure has been folded back and the second connecting portion has been formed, in the second-connecting-portion forming step.

In the present embodiment, as shown in FIG. 9A, at first, a hot-melt adhesive 907 for the second-connecting-portion formation is applied to predetermined positions on the top surface of the single-layered portions in the belt-shaped sheet members 902 with a hot-melt adhesive application means for the second-connecting-portion formation (not shown). Subsequently, as shown in FIG. 9B, the three-layered portions 906 are folded back upward and outward in the width direction with the vicinities of the inner edges in the first connecting portions 11a as starting points, and the bottom layers in the folded-back three-layered portions 906 are joined to the single-layered portions 905 with a hot-melt adhesive 907 for the second-connecting-portion formation, thereby forming the second connecting portions 11b.

Moreover, in the vicinities of both ends of the longitudinal direction of the sanitary napkin 1, all of the three layers of the three-layered portions 906 and the belt-shaped surface sheet 200 are joined in the regions in which the hot-melt adhesive 907 for the second-connecting-portion formation has been applied with a heat sealing means (not shown). That is to say, in the central portion of the longitudinal direction of the sanitary napkin 1, only the bottom layers of the three-layered portions 906 are joined to the belt-shaped surface sheet 200, and upper two layers of the three-layered portions 906 are joined to each other via the plurality of elastic members 13. The bottom layer and the two other layers are separable in the three-layered portions 906. The hollow portion is formed between the bottom layer and the two other layers, which are separable in the three-layered portion 906. On the other hand, in the vicinities of both ends of the longitudinal direction of the sanitary napkin 1, the bottom layers of the three-layered portions 906 are joined to the belt-shaped surface sheet 200 with the hot-melt adhesive 907 for the second-connecting-portion formation, and all of the three layers of the three-layered portions 906 and the belt-shaped surface sheet 200 are joined by heat sealing.

(g) Third-Connecting-Portion Forming Step

In the third-connecting-portion forming step, the three-layered portions and the single-layered portions are joined more outward in width direction than the second connecting portions in the vicinities of both ends of the longitudinal direction of the sanitary napkin 1, thereby forming the third connecting portions.

Figure 10A:
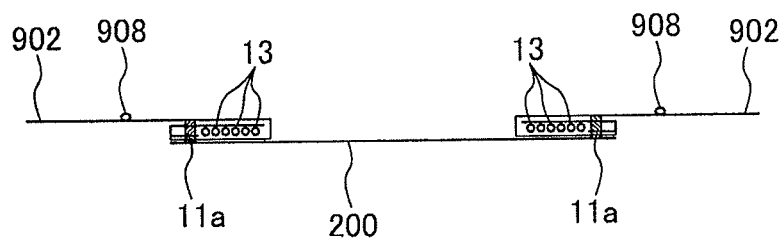
FIG. 10A shows the vicinity of the front edge of the sanitary napkin in a state where a hot-melt adhesive for forming a third connecting portion has been applied in a third-connecting-portion forming step.
Figure 10B:
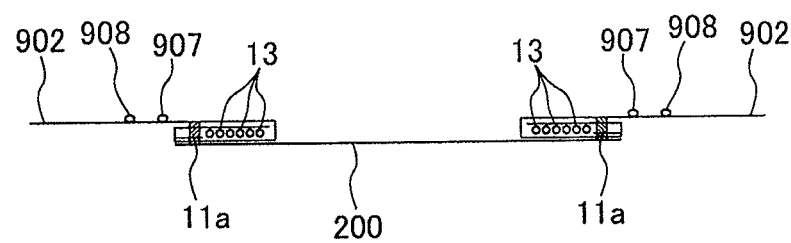
FIG. 10B shows the vicinity of the front edge of the sanitary napkin in a state where the hot-melt adhesive for forming the second connecting portion has been applied to the inside of the width direction after the hot-melt adhesive for forming the third connecting portion has been applied.
Figure 10C:
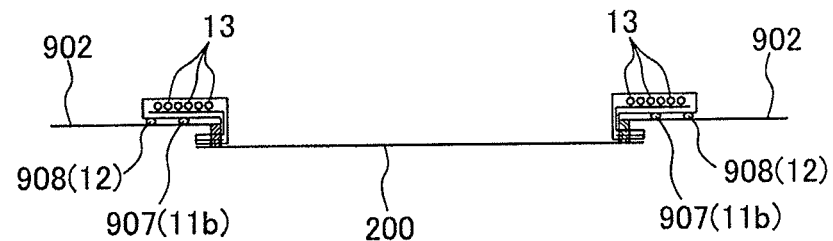
FIG. 10C shows the central portion of the sanitary napkin in a state where the three-layered structure has been folded back and the second and the third connecting portion has been formed.

In the present embodiment, as shown in FIG. 10A and FIG. 10B, after a hot-melt adhesive 908 for the third-connecting-portion formation is applied, a hot-melt adhesive 907 for the second-connecting-portion formation is applied inward in the width direction of the region in which the hot-melt adhesive 908 for the third-connecting-portion formation has been applied. In the vicinities of both ends of the longitudinal direction of the sanitary napkin 1, together with the formation of the second connecting portions, the third connecting portions are formed outward in the width direction (see FIG. 10C).

Figure 11A:
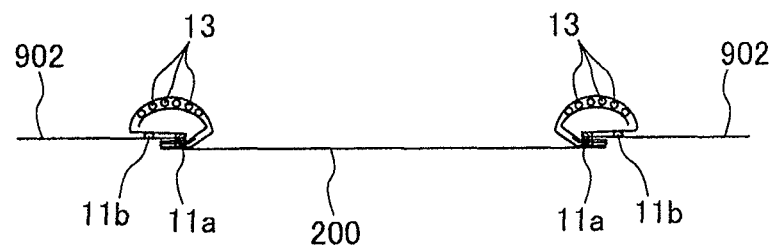
FIG. 11A shows the central portion of the sanitary napkin after the third-connecting-portion forming step.
Figure 11B:
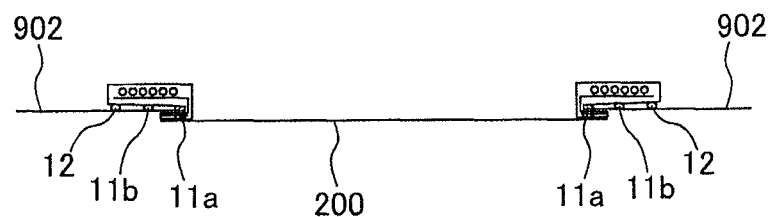
FIG. 11B shows the vicinity of the front edge of the sanitary napkin after a third-connecting-portion forming step.

In this way, the surface layer in the sanitary napkin 1 of the present embodiment is formed, including the surface sheet 2 and the pair of sheet members 9 and 9 (see FIG. 11A and FIG. 11B).

Subsequently, the sanitary napkin 1 of the present embodiment is formed through the laminating step (not shown) in which the absorbent layer and the back layer are laminated on the under surface of this surface layer to form a sanitary napkin continuum, and the cutting step (not shown) in which the sanitary napkin continuum is cut into a shape of the individual sanitary napkins.

According to the present embodiment, it is possible to efficiently manufacture the sanitary napkin 1, in which the plurality of elastic members 13 are arranged in an expanded state to the sheet members 9, and which is provided with the three-dimensional gathers 5 having the hollow portion.

Moreover, in (e) the first-connecting-portion forming step, as shown in FIG. 6, the first connecting portions 11a are formed more outward in the region in which the central portion of the longitudinal direction of the sanitary napkin 1 is located, than in the regions in which the vicinities of both ends of the longitudinal direction of the sanitary napkin 1 are located. Accordingly, as for the sanitary napkin 1 to be manufactured, it is possible to widen the area, in which the absorption is possible by the absorbent layer, in the central portion in the longitudinal direction thereof.

Moreover, in (e) the first-connecting-portion forming step and (f) the second-connecting-portion forming step, the first connecting portions 11a and the second connecting portions 11b are formed in such a way that the ratio (L1/L2) of the length L1 from the first connecting end 10a to the second connecting end 10b in the sheet members 9 and the distance L2 between the first connecting end 10a and the second connecting end 10b is not less than 2, thereby making it possible to easily form the gathers 5 respectively having the three-dimensional-shaped portions 10.

Construction materials of the sanitary napkin 1 of the present embodiment are described.

As the surface sheet 2, it is possible to use nonwoven fabrics with or without pores or porous plastic sheets. As the back sheet 3, it is possible to use a hydrophobic nonwoven fabric, an impermeable plastic film, or a laminated sheet of the nonwoven fabric and the impermeable plastic film. Alternatively, as the back sheet 3, it is also possible to use a SMS nonwoven fabric sandwiched by melt-blown nonwoven fabrics having high water-resisting property and high-strength spun-bonded nonwoven fabrics.

As the absorbent body 4, it is possible to use a fluff pulp or an airlaid nonwoven fabric as well as a high-absorbance polymer.

Examples of the fluff pulp to be used as the absorbent body 4 include chemical pulps, cellulose fibers, and artificial cellulose fibers such as rayon and acetate. Examples of the airlaid nonwoven fabric include one prepared by thermal fusion of a pulp with a synthetic fiber or fixing them by a binder. Examples of the high-absorbance polymer include starch-, acrylic acid-, and amino acid-based granular or fibrous polymers.

As the sheet members 9, water-repellent or hydrophobic materials are preferably used. Specifically, it is possible to use various non-woven fabrics such as spun lace non-woven fabrics, spun bond nonwoven fabrics, thermal bond non-woven fabric, meltblown non-woven fabrics, needle-punched nonwoven, and air through non-woven fabrics. As raw material fibers which constitute the nonwoven fabrics, it is possible to use olefin (such as polyethylene or polypropylene)-, polyester-, and polyamide-based synthetic fibers, as well as regenerated fibers such as rayon and cupra, and natural fibers such as cotton.

As the elastic members 13, it is acceptable as long as it is a stretching and contracting material, and it is possible to use filar rubber or flat rubber constituted of natural rubber, and thermoplastic elastomer such as urethane, ethylene-vinyl acetate copolymer (EVA) and PE. More specifically, examples of the thermoplastic elastomer include ones in which any of the following materials is shaped into a filar or film shape and slit into a narrow width: polybutadiene, polyisoprene, styrene-butadiene copolymer, styrene-isoprene copolymer, polyurethane, ethylene-acetic acid vinyl copolymer, and ethylene-alpha olefin copolymer.

The sanitary napkin 1 of the present embodiment having the configuration as described above is fixed to the underwear in such a way that the elongated main-body portion is arranged at the inner face of the crotch area of the underwear such as undergarment, and the pair of wings 6 and 6 are folded back to the outer side of the crotch area. The sanitary napkin 1 is fixed to the underwear in such a way that the main-body adhesive parts 15 arranged on the under surface of the main-body portion are fastened to the inner face of the crotch area, and the wing adhesive parts 14 and 14 arranged on the under surface of the pair of wing 6 and 6 are fastened to the outer surface of the crotch area.

In the sanitary napkin 1 of the present embodiment having the configuration as described above, in the three-dimensional-shaped portion 10 forming the gather 5, the ratio of the length L1 from the first connecting end 10a to the second connecting end 10b and the distance L2 between the connecting ends, which is the distance between the first connecting end 10a and the second connecting end 10b, is not less than 2, as a result of which the three-dimensional shape of the pair of gathers 5 and 5 is stably formed, and the gathers 5 are less likely to collapse even in cases where forces are applied to the sanitary napkin 1 from the width direction. Moreover, since the inside of the three-dimensional shape of the gathers 5 is hollow, it is possible for the gathers 5 to fit, in a planar form, with the wearer's body, and it is also possible for the three-dimensional shape of the gathers 5 to flexibly follow the physical motion of the wearer, thereby making it possible to effectively prevent leakage from width direction of the sanitary napkin 1. Furthermore, in cases where the forces are applied to the sanitary napkin 1 from the width direction, the gathers 5 of the three-dimensional shape having the hollow portion absorb and buffer the applied forces, thereby making it possible to reduce the forces applied to the absorbent body 4. As a result, the absorbent body 4 is hard to deform, and the fitness of the sanitary napkin 1 to the wearer's body is improved.

Moreover, the cross-sectional shape of the gathers 5 in the width direction is substantially $\Omega$-shaped, in which the largest width L3 of the three-dimensional shape of the gathers 5 is greater than the distance L2 between the connecting ends, as a result of which the standability of the gathers 5 is improved.

Furthermore, the connecting portion 11 includes a first connecting portion 11a which is formed inward in the width direction of the sanitary napkin 1, and a second connecting portion 11b which is formed more outward in the width direction than the first connecting portion, in which the first connecting end 10a is formed in the first connecting portion 11a, and in which the second connecting end 10b is formed in the second connecting portion 11b. In this way, the first connecting end 10a and the second connecting end 10b are formed at connecting portions which are different (separated) from each other, thereby the inner sides 5a of the gathers 5 are less likely to receive influence of the forces applied in the width direction, and the gathers 5 are less likely to collapse, as a result of which the effect of preventing the side leakage is also improved.

Moreover, the distance L2b between the connecting ends in the vicinities of both ends in the longitudinal direction of the sanitary napkin 1 is greater than the distance L2a between the connecting ends in the central portion in the longitudinal direction of the sanitary napkin 1, as a result of which the tension to the gathers 5 in the width direction is gradually increased from the central portion to the both ends. This improves the standing stability of the gathers 5 of the three-dimensional shape, and makes the gathers 5 to be less likely to collapse.

Furthermore, the third connecting portions 12, which join the sheet members to the surface layer or the back layer more outward in the width direction than the connecting portion, are respectively formed at both ends of the longitudinal direction the pair of gathers 5 and 5. The distance L4 between the outer end in the third connecting portion 12 and the first connecting end 10a is longer than the distance L2a between the connecting ends in the longitudinal direction of the central portion of the sanitary napkin 1. Accordingly the tension to the gathers 5 in the width direction is further increased from the central portion to the both ends. This improves the standing stability of the gathers 5 of the three-dimensional shape, and makes the gathers 5 to be less likely to collapse.

Moreover, the center in the width direction of the connecting portion 11 is located more inward in the width direction than the center between the outer end in the third connecting portion 12 and the first connecting end 10a, as a result of which the three-dimensional shape of the gathers 5 has the substantial $\Omega$-shape that is declined outward in the width direction from the lower end to the upper end. That is to say, the pair of gathers 5 and 5 are arranged in such a way that the distance between the top ends is greater than the distance between the bottom ends. The pair of gathers 5 and 5 are arranged in such a way that the distance between the top ends is greater than the distance between the bottom ends, thereby improving the effect of preventing the side leakage of the sanitary napkin 1.

Moreover, the first connecting end 10a is located in a region to be arranged on the absorbent layer in the surface layer, and the second connecting end 10b is located in a region on the back layer, outward to the external margin of the absorbent layer in the width direction. Because of the presence of the thick absorbent body 4, the rigidity is higher in regions in which the first connecting ends 10a are located on the absorbent layer in the surface layer, than in regions in which the second connecting ends 10b are located. Therefore, regions of the inner sides 5a located on the sides of the first connecting ends 10a in the gathers 5 are less likely to be affected by the forces, which are applied to the sanitary napkin 1 in the width direction, than regions of the outer sides 5c located on the sides of the second connecting ends 10b. As a result, in cases where forces are applied to the sanitary napkin 1 from the width direction, the shape of the inner sides 5a in the gathers 5 is easily changed, thereby absorbing the applied forces. Accordingly, the shape of the outer sides 5c in the gathers 5 is stable, thereby making it possible to improve the effect of preventing the side leakage.

Particularly in cases where the wings are folded back to be fastened to the outer side of the crotch area such as undergarment, the wigs are pulled outward to the width length. As a result, in the conventional gathers, the article is worn in a state where the gathers are collapsed due to this outward tension to the width direction, thereby leading to the side leakage. However, according to the sanitary napkin 1 of the present embodiment, in the cases where the forces are applied to the sanitary napkin 1 from the width direction in this way, the shape of the outer side 5c in the gathers 5 is easily changed to absorb the applied forces, as a result of which the shape of the inner sides 5a in the gathers 5 is stable, thereby making it possible to improve the effect of preventing the side leakage.

Moreover, each of the pair of gathers 5 and 5 have the plurality of elastic members 13, and the plurality of elastic members 13 are arranged on the surface of, or inside, the sheet members 9, and are arranged along the longitudinal direction, thereby making it possible to stably maintain the three-dimensional shape having the hollow portion of gather 5.

Moreover, all or part of the plurality of elastic members 13 is arranged to the respective sides of the pair of gathers 5 and 5, thereby making it possible to more stably maintain the three-dimensional shape having the hollow portion of gather 5.

Furthermore, each of the pair of gathers 5 and 5 has the two-layered portion which is formed by folding back the sheet member 9, and the plurality of elastic members 13 are arranged in such a way to be interposed between the layers of the two-layered portion, as a result of which the gathers 5, in which the plurality of elastic members 13 are arranged, have appropriate rigidity, thereby improving the standing stability of the gathers 5.

In addition, the leak-proof groove portion 8 has a shape which is convexly curved outward in the width direction in the central portion A. Accordingly, in cases where the sanitary napkin 1 receives forces from the width direction, the standing stability of the gathers 5 is improved in the central portion A which is a region corresponding to the excretion part, thereby improving the effect of preventing the side leakage. Furthermore, the absorbent body 4 is more likely to be lifted up on the skin contacting side of the wearer as a result of the forces applied from the width direction, thereby creating an effect of improving the contact between the absorbent body 4 and the excretion part of the wearer.

The present invention is not limited to the above described embodiments, but various alterations are possible within a scope of the present invention.

For example, in the present embodiment, as for the pair of gathers 5 and 5, the plurality of elastic members are arranged to the sheet members 9, but instead of using the plurality of elastic members, seats having contraction and expansion properties may be used as the sheet members 9. Moreover, the pair of gathers 5 and 5 may be formed with sheet members which do not have contraction and expansion properties.

Furthermore, in the present embodiment, the gathers 5 and the wings 6 are formed with one piece of the sheet member 9, but the wings 6 may be configured with seats which are different from the seat members 9 constituting the gathers 5.

The absorbent article of the present invention may be, in addition to sanitary napkins, urine-absorbing pads, panty liners, disposable diaper and the like.

The invention claimed is:

1. An elongated absorbent article, comprising:
a surface layer having an at least partly liquid-permeable surface sheet;
a back layer having a liquid-impermeable back sheet;
an absorbent layer having a liquid-retainable absorbent body arranged between the surface and back layers;
a pair of gathers which are formed to be separated from each other in both sides along a longitudinal direction in the surface layer and are formed all across an anterior portion, a central portion and a posterior portion of the absorbent article extending in the longitudinal direction of the absorbent article, and which are configured to have a hollow portion in a three-dimensional-shaped portion which is convex on a skin contacting side of the absorbent article, formed with a sheet member having a connecting portion formed to extend in the longitudinal direction of the absorbent article,
wherein the connecting portion includes a first connecting end and a second connecting end that are disposed between an inward edge and an outward edge of the hollow portion in a width direction of the three-dimensional-shaped portion,
wherein, in the three-dimensional-shaped portion, a ratio (L1/L2) of a length L1 from the first connecting end along a surface of the gather to the second connecting end and a distance L2 between the first connecting end and the second connecting end is not less than 2, a cross-sectional shape of the gather in the width direction is a substantially Ω-shape, in which a largest width L3 of the three-dimensional-shaped portion of the gathers is greater than the distance L2 between the first and second connecting ends, and
wherein the distance between the first connecting end and the second connecting end at a side of the anterior portion and the posterior portion is greater than the distance between the first connecting end and the second connecting end in the central portion,
wherein a plurality of elastic members is included in the pair of gathers extending in the longitudinal direction of the absorbent article to maintain the substantially Ω-shape, and the plurality of elastic members are arranged at an inner side, a top side and an outer side of the three-dimensional shape of the pair of gathers, and
wherein each of the pair of gathers has a two-layer portion which defines the hollow portion, and the two-layer portion is formed in such a way that the sheet member extends from a region more outward in the width direction than an outer edge of the absorbent body to an upper surface of an end of the absorbent body, is folded back outwardly at a first folding back portion, extends along an outer side, a top side and an inner side of the three-dimensional-shaped portion, is folded back inwardly at a second folding back portion, and extends along an inner periphery of the hollow portion within the three-dimensional-shaped portion;

wherein the first connecting end comprises the first and second folding back portions that are overlapped and joined to each other, and the second connecting end is comprises a region in which opposed surfaces of the sheet member adjacent to the first folding back portion are joined to each other.

2. The absorbent article according to claim 1,
wherein the ratio (L1/L2) is between 2 to 15 and the ratio (L1/L2) of the central portion is greater than that of each of the first connecting end and the second connecting end.

3. The absorbent article according to claim 1,
wherein the connecting portion has a first connecting portion which is formed inward in the width direction of the absorbent article, and a second connecting portion which is formed more outward than the first connecting portion in the width direction, and wherein the first connecting end is formed in the first connecting portion, and the second connecting end is formed in the second connecting portion.

4. The absorbent article according to claim 3,
wherein third connecting portions, which join the sheet member to the surface layer or the back layer more outward in the width direction than the second connecting portion, are respectively formed at the anterior portion and the posterior portion of the longitudinal direction in the pair of gathers, and wherein a distance between an outer end in the third connecting portion and the first connecting end is longer than the distance between the first and second connecting ends in the longitudinal direction of the central portion of the absorbent article.

5. The absorbent article according to claim 1,
wherein the plurality of elastic members are arranged on a surface, or inside, of the sheet member, and are arranged along the longitudinal direction.

6. The absorbent article according to claim 5,
wherein no less than two of the plurality of elastic members are arranged at an outer side, which is located outward in the width direction, among sides in the pair of gathers, wherein the no less than two of the plurality of elastic members has a first elastic member, which is arranged the most closely to the second connecting end, and a second elastic member, which is adjacent to the first elastic member, and wherein the second elastic member is located more outward in the width direction than the first elastic member.

7. The absorbent article according to claim 5,
wherein each of the plurality of elastic members has a chromatic color, and wherein the chromatic color in each of the plurality of elastic members is visible through the sheet member.

8. The absorbent article according to claim 1,
wherein the first connecting end is located in a first region where the surface sheet is arranged on the absorbent body, and wherein the second connecting end is located in a second region where the absorbent body is not arranged below thereof, and a rigidity of the second region is lower than that of the first region.

9. An elongated absorbent article, comprising:
a surface layer having an at least partly liquid-permeable surface sheet;
a back layer having a liquid-impermeable back sheet;
an absorbent layer having a liquid-retainable absorbent body arranged between the surface and back layers;
a pair of gathers which are formed to be separated from each other in both sides along a longitudinal direction in the surface layer and are formed all across an anterior portion, a central portion and a posterior portion of the absorbent article extending in the longitudinal direction of the absorbent article, and which are configured to have a hollow portion in a three-dimensional-shaped portion which is convex on a skin contacting side of the absorbent article, formed with the sheet member having a connecting portion formed to extend in the longitudinal direction of the absorbent article, wherein the connecting portion includes a first connecting end and a second connecting end that are disposed between an inward edge and an outward edge of the hollow portion in a width direction of the three-dimensional-shaped portion, wherein, in the three-dimensional-shaped portion, a ratio (L1/L2) of a length L1 from the first connecting end along a surface of the gather to the second connecting end and a distance L2 between the first connecting end and the second connecting end is not less than 2, a cross-sectional shape of the gather in the width direction is substantially Ω-shape, in which a largest width L3 of the three-dimensional-shaped portion of the gathers is greater than the distance L2 between the first and second connecting ends, wherein the distance between the first connecting end and the second connecting end at a side of the anterior portion and the posterior portion is greater than the distance between the first connecting end and the second connecting end in the central portion, wherein a plurality of elastic members is included in the pair of gathers extending in the longitudinal direction of the absorbent article to maintain the substantially Ω-shape, the plurality of elastic members are arranged to at inner side, a top side and an outer side of the three-dimensional-shaped portion of the pair of gathers, wherein each of the pair of gathers has a two-layer portion which defines the hollow portion, and the two-layer portion is formed in such a way that the sheet member extends from a region more outward in the width direction than an outer edge of the absorbent body to an upper surface of an end of the absorbent body, is folded back outwardly at a first folding back portion, extends along an outer side, a top side and an inner side of the three-dimensional-shaped portion, is folded back inwardly at a second folding back portion, and extends along an inner periphery of the hollow portion within the three-dimensional-shaped portion;

wherein the first connecting end comprises the first and second folding back portions that are overlapped and joined to each other, and the second connecting end is comprises a region in which opposed surfaces of the sheet member adjacent to the first folding back portion are joined to each other, wherein the plurality of elastic members has a first elastic member, which is disposed most closely to the second connecting end, a second elastic member, which is adjacent to the first elastic member, and a third elastic member, which is adjacent to the second elastic member, and wherein the second elastic member is disposed in the outermost position in the width direction of the three-dimensional-shaped portion, and the first elastic member and the third elastic member are located inward thereof.

10. The absorbent article according to claim 9,
wherein the first connecting end is located in a first region where the surface sheet is arranged on the absorbent body, and
wherein the second connecting end is located in a second region where the absorbent body is not arranged below thereof, and a rigidity of the second region is lower than that of the first region.

* * * * *